(12) United States Patent
Helmke et al.

(10) Patent No.: US 8,968,718 B2
(45) Date of Patent: Mar. 3, 2015

(54) BIOREMEDIATION METHOD FOR ACCELERATED BIOLOGICAL DECOMPOSITION OF PETROLEUM HYDROCARBONS IN SEA ICE-COVERED POLAR REGIONS, AND BACTERIA AND ENZYME MIXTURES AS AGENTS FOR CARRYING OUT SAID METHOD

(71) Applicant: Stiftung Alfred-Wegener-Institut fuer Polar-Und Meeresforschung, Bremerhaven (DE)

(72) Inventors: Elisabeth Helmke, Bremerhaven (DE); Birte Gerdes, Bremerhaven (DE); Jutta Juergens, Bremerhaven (DE); Kristine Reuter, Langen (DE)

(73) Assignee: Alfred-Wegener-Institut Helmholtz-Zentrum fuer Polar-und Meeresforschung, Bremerhaven (DE)

( * ) Notice: Subject to any disclaimer, the term of this patent is extended or adjusted under 35 U.S.C. 154(b) by 0 days.

(21) Appl. No.: 13/848,901

(22) Filed: Mar. 22, 2013

(65) Prior Publication Data
US 2013/0210112 A1   Aug. 15, 2013

Related U.S. Application Data

(62) Division of application No. 12/523,818, filed as application No. PCT/DE2008/000018 on Jan. 6, 2008, now Pat. No. 8,444,962.

(30) Foreign Application Priority Data

Jan. 21, 2007   (DE) .......................... 10 2007 003 644

(51) Int. Cl.
| | | |
|---|---|---|
| *A01N 63/00* | (2006.01) | |
| *C02F 3/34* | (2006.01) | |
| *B09C 1/10* | (2006.01) | |
| *C02F 3/12* | (2006.01) | |
| *C12P 39/00* | (2006.01) | |
| *C12R 1/01* | (2006.01) | |
| *C02F 1/40* | (2006.01) | |
| *C02F 101/32* | (2006.01) | |
| *C02F 103/08* | (2006.01) | |

(52) U.S. Cl.
CPC . *C02F 3/341* (2013.01); *B09C 1/10* (2013.01); *C02F 3/12* (2013.01); *C02F 3/342* (2013.01); *C02F 3/343* (2013.01); *C12P 39/00* (2013.01); *C12R 1/01* (2013.01); *C02F 1/40* (2013.01); *C02F 2101/32* (2013.01); *C02F 2103/08* (2013.01); *C02F 2301/103* (2013.01); *C02F 2305/06* (2013.01)
USPC ..... 424/93.1; 435/183; 435/252.1; 435/252.4

(58) Field of Classification Search
None
See application file for complete search history.

(56) References Cited

U.S. PATENT DOCUMENTS

| 5,954,868 A | 9/1999 | Felix et al. |
| 5,965,431 A | 10/1999 | Maerkl et al. |

FOREIGN PATENT DOCUMENTS

| DE | 3811856 A1 | 3/1989 |
| DE | 4443266 A1 | 6/1995 |
| DE | 19652580 A1 | 7/1998 |
| DE | 19954643 A1 | 6/2001 |
| DE | 102005028295 A1 | 11/2006 |
| EP | 0859747 B1 | 8/1998 |
| JP | 2004181314 A | 7/2004 |
| JP | 2006007542 A | 1/2006 |
| RU | 2107722 C1 | 3/1998 |

OTHER PUBLICATIONS

Rike, et al, 2005 "In situ biodegradation of hydrocarbons in arctic soil at sub-zero temperatures—filed monitoring and theoretical simulation of the microbial activation temperature at a Spitsbergen contaminated site," Cold Regions Science and Technology 41 : 189-209.
Brakstad, et al, 2006 "Biodegradation of petroleum hydrocarbons in seawater at low temperatures (0-5° C.) and bacterial communities associated with degradation," Biodegradation 17: 71-82.
Rahman, et al, 2006 "Biodegradation of Hydrocarbon Contamination by Immobilized Bacterial Cells" Journal of Microbiology 44(3): 354-359.
Margesin, et al, 1999 "Biological decontamination of oil spills in cold environments," J. Chem. Technol Bictechnol 74: 381-389.
Deppe, et al, 2005 . "Degradation of crude oil by an arctic microbial consortium," Extremophiles 9: 461-470.
Priscu, et al, 1998 "Perennial Antarctic Lake Ice: An Oasis for Life in a Polar Desert" Science 280: 2095-2098.
International Search Report for PCT/DE2008/000018 Mail date Sep. 9, 2008.
ARCOP 04.2.1.1 (a), Kapitel 4 "Oil spill response-present alternatives for ice covered water" pp. 29-88, 2004.
B. Gerdes et al. "Influence of crude oil on changes of bacterial communities in Arctic sea-ice", FEMS Microbiology Ecology 53 (2005) pp. 129-139.
Zhu et al. "Literature review on the use of commercial bioremediation agents for cleanup of oil-contaminated estuarine environments" Bericht EPA/600/R-04/075, Jul. 2004, pp. 1-61.
Delille at al. "Seasonal Variation of Bacteria in Sea Ice Contaminated by Diesel Fuel and Dispersed Crude Oil", Microb. Ecol. (1997), 33, pp. 97-105.
B. Gerdes at al, (WP4 Environmental Protection, "Biological degradation of crude oil in Artic sea ice", ARCOP Workshop 8, Oct. 19-20, 2005, St. Petersburg, pp. 1-15.

*Primary Examiner* — Kade Ariani
(74) *Attorney, Agent, or Firm* — Leydig, Voit & Mayer, Ltd.

(57) ABSTRACT

A bacterial mixture usable in an inoculum usable in a biore-mediateion method for accelerated biological degradation of petroleum hydrocarbons in a sea ice-covered polar region includes a plurality of isolated cold-adapted autochthonous bacterial strains. Each of the bacterial strains has petroleum hydrocarbons degrading activity at an ambient temperature of −3° C. and each has a different temperature tolerance range, a different salinity tolerance range, a different petroleum hydrocarbons degradation spectrum, and a different capacity to emulsify oil.

5 Claims, No Drawings

BIOREMEDIATION METHOD FOR ACCELERATED BIOLOGICAL DECOMPOSITION OF PETROLEUM HYDROCARBONS IN SEA ICE-COVERED POLAR REGIONS, AND BACTERIA AND ENZYME MIXTURES AS AGENTS FOR CARRYING OUT SAID METHOD

CROSS REFERENCE TO PRIOR APPLICATIONS

This application is a division of U.S. application Ser. No. 12/523,818 which hereby is incorporated by reference herein and which is a U.S. National Phase application under 35 U.S.C. §371 of International Application No. PCT/DE2008/000018, filed Jan. 6, 2008 and claims benefit to German Patent Application No. DE 10 2007 003 644.4, filed Jan. 21, 2007. The International Application was published in German on Jul. 31, 2008 as WO 2008/089718 under PCT Article 21(2).

FIELD

The present invention relates to a bioremediation method for accelerated biological degradation of petroleum hydrocarbons in sea ice-covered polar regions by bioaugmentation with exogenous, hydrocarbon-degrading bacteria and addition of nutrients, and further relates to bacterial mixtures and enzymes obtainable therefrom for degrading hydrocarbons as means for carrying out the method.

BACKGROUND

Due to the increasing exhaustion of the currently exploited oil deposits (petroleum hydrocarbons), oil prospection efforts are presently tending towards extreme places. In this connection, the Arctic Ocean and its marginal seas, the Arctic shelf regions, and the Arctic permafrost regions, which are assumed to contain about 25% of the world's oil and gas reserves, are also increasingly moving into the focus of interest. In some places, oil is already being extracted in significant amounts.

The central Arctic Ocean is covered throughout the year with sea ice, which can be thick in some areas. In the Arctic marginal seas and the shelf and coastal regions, drift ice or a closed sea-ice cover is present at least during the colder seasons of the year. Extraction platforms which are set up in these regions are subject to particular loads caused by drifting ice. Another problem is material fatigue caused by very low temperatures. This is true, for example, for the submarine pipelines that lead to the anchorage sites of the ships in the shelf region. Transporting oil through the ice by ship also involves increased risks, so that the risk of oil contamination or ship accidents is much higher in this region than in temperate or tropical latitudes. In polar ice regions, in addition to single oil spills caused, in particular, by ship or other accidents, there is also a high risk of continuous oil spills, which may be caused, for example, by oil extraction from platforms, or during loading operations for oil transports, or by leaks in burst-prone pipelines.

The oil removal measures so far employed in free water can only be used to a limited extent in polar ice regions, because the distribution of oil in ice differs significantly from that in water. Only frazil ice behaves similarly to water. A problem in the development of methods for oil removal in sea ice-covered regions lies in the different ice conditions. There is no uniform ice cover, and therefore no method which could be generally used in ice. Ice conditions vary from ice platelets, frazil ice, young pancake ice, and larger ice floes, up to a closed ice cover. The measures for ice removal are not only dependent on the consistency of the ice and the floe size and thickness, but also on the dynamics of the ice field, on the weather, and on the swell of the water between the floes. The oil slick may get under the ice or smeared over the ice floes, be frozen into the ice, or mix homogeneously with the frazil ice. Generally, it can be said that the separation of oil and ice becomes very difficult once the oil gets into the ice. It is still easier if the oil concentrates between ice floes in the water, but even then it is not possible to use all of the methods usually used in water, because most equipment (e.g., oil barriers) cannot be maneuvered in areas of ice floes.

To date, no minor or major spills are known to have occurred in sea ice-covered regions. However, since the risk of oil spills is on the rise and the natural cleansing capacity of these ecosystems is known to be significantly lower than in other places because of the very low temperatures prevailing there, it is becoming increasingly urgent to develop effective measures and methods for cleaning up oil spills in sea ice-covered areas. The current state of the art in the field of oil spill recovery in ice-covered areas is described extensively in a report of July 2004 issued by the ARCOP project of the European Union (ARCOP D4.2.1.1 (a), Chapter 4 "Oil spill response—present alternatives for ice covered water" pp 29-88). The report presents possible methods (see below) and their advantages and disadvantages. Some of the presented methods and tools have been tested in small studies, but have not yet been used in emergency situations.

Mechanical methods, which all amount to a kind of "washing principle", make up the major part of the proposed oil removal methods. However, these methods are only suitable for cleaning smaller ice floes. Oil residues remain in the ice. In all mechanical schemes, the biology of the environment is severely affected, in most cases even completely destroyed. Regeneration occurs at a very slow pace.

Burning of oil in ice, which is generally referred to as "in-situ burning", is a method which can only be used either when the degree of ice coverage is low or when it is very high. The oil content in the ice must exceed 25 percent in order for the oil to burn off The removal of oil is fast and effective. This method has the disadvantage that the heat produced completely destroys the ecosystem, so that afterwards there is hardly any chance for residual contamination to be eliminated by natural biological degradation. Moreover, the emissions and combustion residues may have toxic effects even at places relatively far from the burning site.

Chemical methods are of limited suitability for use in ice due to the lack of effective mixing, which is only possible if a small number of ice floes are in turbulent water. Moreover, many of the chemical dispersants are toxic and, therefore, most of them are forbidden in Germany. Besides, the oil is actually not removed; rather, the problem is merely displaced, because dispersed oil can spread more easily.

Biological methods can theoretically be used in ice. However, to date, they have not been used in practice, because experts consider it impossible for oil to be effectively biodegraded at the low unphysiological temperatures in ice. A small population of hydrocarbon degraders could, in fact, be identified in the ice; but these were only short-chain alkane degraders (B. Gerdes et al. "Influence of crude oil on changes of bacterial communities in Artie sea-ice", FEMS Microbiology Ecology 53 (2005) pp 129-139). Inoculation of oil degraders in ice is also problematic because the temperature and salinity conditions are not only extreme, but also highly variable.

In general, biological methods, also known as bioremediation methods, are very environmentally friendly, and are frequently used in prior art methods in warmer areas, especially for soil clean-up purposes. Such methods promote the development of the natural, oil-degrading microbial community by adding nutrients to compensate for the lack of nitrogen and phosphates, thereby accelerating the natural degradation process. To date, this technology has been successfully used not only in soils but also in near-coast waters, and even in cold waters, for example during the Exxon Valdez disaster in the Arctic waters off the coast of Alaska. Apart from the addition of nutrients, experiments were also conducted on the addition of oil-degrading bacteria. To date, however, this inoculation method has proved successful only in closed systems or containers (ex-situ methods, for example for cleaning up excavated soils), but not in free nature. When types of bacteria were used which normally do not live in the contaminated place, such bacteria were mostly unable to compete with the specific, well-adapted autochthonous flora (Zhu et al. "Literature review on the use of commercial bioremediation agents for cleanup of oil-contaminated estuarine environments", EPA report no. EPA/600/R-04/075 July 2004). Also, generally only a single type of hydrocarbon-degrading bacteria was used, for example one of the genus *Pseudomonas* (DE 38 11 856 C2), *Bacillus* (DE 196 52 580 A1), or *Acetobacter* (DE 44 43 266 A1). In the most favorable case, the degradation was accelerated for a short period of time. After about 2 weeks, the inoculated organisms were grown over with autochthonous flora.

In Japanese abstracts JP 2004181314 A and JP 200607542 A, it is proposed to use natural bacterial mixtures for soil clean-up purposes. However, unlike sea ice, soils are relatively homogenous and stable habitats, in which organisms are not exposed to a physical-chemical gradient as strong as that in sea ice. In addition, the introduced bacteria cannot be washed out so easily. Furthermore, European document EP 0 859 747 B1 discloses a method for aerobic biodegradation of substances having low water solubility. This method uses a culture of the thermophilic microorganism designated IHI-91 (DSM 10561). This strain is very similar to the genus Bacillus. The scope of protection of this European patent encompasses the microorganism IHI-91 itself and the enzyme composition obtainable therefrom for biodegradation purposes. The document DE 196 52 580 A1 referred to earlier herein does, in fact, mention a "bacterial mixture" for regenerating soils and waters contaminated by crude oil and/or oil products. In addition to the bacterial genus *Bacillus*, there is also used an unspecific "biosurfactant BS-4", which is produced by hydrolysis of micro-biomass (waste). It is not clear whether additional types of bacteria are contained therein. However, due to the strong chemical hydrolysis, it can be assumed that the mixture contains only one bacterial genus. Finally, German document DE 199 54 643 A1 discloses the manufacture and use of an oil binder for removing all kinds of oils and fats from water surfaces and solid surfaces. Microorganisms are immobilized on fiber-forming proteins in granular form. These microorganisms may be of the type *Pseudomonas putida, Pseudomonas* spec., *Acinetobacter calcoaaceticus, Nocardia* spec., *Corynebacterium* spec., *Candida lipolytica, Candida tropicalis, Rhodopseudomonas palistris* or *Rhodococcus* spec. It is not described whether bacterial mixtures are immobilized. Also, no specific information is provided concerning the selection of the microorganisms mentioned. The immobilization of microorganisms is not included in any of the exemplary embodiments described.

All of the aforementioned publications have in common that they describe the biological degradation of oil by bacteria of different genus and species only at normal or even elevated ambient temperatures (thermophilic bacteria), but not at low temperatures (by definition, cold-adapted bacteria are organisms that have a minimum growth temperature of 0° C. or lower; the group of cold-adapted organisms being further dividable into what is known as "psychrophilic organisms", which have a maximum growth temperature below 20° C., and the "psychrotolerant organisms", which have a maximum growth temperature above 20° C. German document DE 10 2005 028 295 A1 describes only the use of psychrophilic proteases of the genus *Shewanella* for removing biofilms from hard surfaces. However, none of the applications described is for the low temperature range around or below the freezing point. Rather, it can be assumed that the use of psychrophilic proteases is aimed at shifting the temperature at which dirt and biofilms are removed from the previously used value of 37° C. to a range between 15 and 20° C. (see paragraphs [006] through [008]). It is not disclosed to remove biofilms under sea-ice conditions.

Sea ice with its extremely low temperatures and highly varying salinities is a hostile environment, which is considered by experts to be unsuitable for bioremediation methods. The only bioremediation experiment in sea ice so far published is that of DeIiIle et al. ("Seasonal Variation of Bacteria in Sea Ice Contaminated by Diesel Fuel and Dispersed Crude Oil", Microb. Ecol. (1997) 33 pp 97-105). Antarctic sea ice was contaminated with Arabian crude or diesel oil, and some of the experimental areas were fertilized with the organic nutrient complex INIPOL EAP 22. An increase in microorganisms was observed both in the fertilized and also in the unfertilized oil-contaminated experimental areas as compared to the control area. However, it was not examined whether and to what extent oil had been degraded, or which components had disappeared. The organisms that were present after the distribution of oil and nutrients were not isolated or characterized. However, the increase in microorganisms suggests that the oil at least does not have a toxic effect on part of the sea-ice community.

As mentioned earlier, the hostile conditions in sea ice, i.e., the very cold temperatures and sometimes very high salinities, and the strong variations in temperature and salinity across the ice floe profile and over the season, stand in the way of using bioremediation methods in such regions. Even in cold-adapted bacteria, microbial growth and activity are low in the temperature range from about −5° C. to −3° C., which is the temperature range prevailing in the lower region of the ice (boundary region between water and ice), and in the region of the ice surface (temperature range from about +1° C. in summer to below −20° C. in winter), microbial growth and activity are even limited to the short summer season. Sea ice is colonized by a specific microbial community which is closely adapted to the particular environment in which they live. Since polar sea ice has so far scarcely been confronted with crude oil, experts have so far considered it quite improbable that a natural, hydrocarbon-degrading flora could occur and quickly develop in the event of an oil spill. On the one hand, these factors speak against the use of bioremediation methods in ice but, on the other hand, it is especially in sea ice that biological methods offer many advantages over physical-chemical methods. They could be used in virtually any ice situation and oil spill scenario, regardless of whether the oil is on the ice, under the ice, or in free water. Moreover, once the nutrients and organisms were applied, they would need no further attention. Thus, it would not be necessary to stay at the site during oil spill recovery operations in difficult-to-access areas. Rather, the system could be left alone once it has been prepared.

The prior art has not proposed any practical bioremediation methods for degrading oil in sea ice regions (see ARCOP D4.2.1.1 (a), Chapter 4 "Oil spill response—present alternatives for ice covered water" pp 29-88, at page 88, chapter 5.6). However, B. Gerdes et al. (WP4 Environmental Protection, "Biological degradation of crude oil in Artic sea ice", ARCOP Workshop 8, 19-20 Oct. 2005, St. Petersburg) describes the possibility of a bioremediation method allowing natural aerobic degradation processes in polar ice regions to be accelerated by bioaugmentation with exogenous microbes and/or addition of nutrients and/or oxygen. Among the degradation-limiting factors mentioned are nutrients, availability of oxygen, temperature, trace elements, such as iron, salinity and pH value, solubility and droplet size of the oil. However, it turned out oil was not able to be significantly degraded during the Arctic winter at temperatures around −3° C., either by fertilization with nutrients, or by inoculation, whereas the bacterial diversity changed significantly at 0° C. in inorganically fertilized melt water samples.

Thus, B. Gerdes et al. (WP4 Environmental Protection, "Biological degradation of crude oil in Artic sea ice", ARCOP Workshop 8, 19-20 Oct. 2005, St. Petersburg), discloses that a bioremediation method for accelerated biological degradation of petroleum hydrocarbons in polar ice regions by bioaugmentation with exogenous, hydrocarbon-degrading bacteria and addition of nutrients is possible at temperatures above the freezing point. It appears that the biodegradation stops below the freezing point. However, no information is provided on the mode of operation of the bioremediation method or on suitable bacterial mixtures as means for carrying out the method.

SUMMARY

In an embodiment, the present invention provides a bacterial mixture usable in an inoculum usable in a bioremediateion method for accelerated biological degradation of petroleum hydrocarbons in a sea ice-covered polar region. The bacterial mixture includes a plurality of isolated cold-adapted autochthonous bacterial strains each having petroleum hydrocarbons degrading activity at an ambient temperature of −3° C. and each having a different temperature tolerance range, a different salinity tolerance range, a different petroleum hydrocarbons degradation spectrum, and a different capacity to emulsify oil.

DETAILED DESCRIPTION

An aspect of the present invention is to improve the above-described bioremediation method in such a way that hydrocarbons, especially in the form of minor oil spills, are biologically degraded under the conditions prevailing in polar ice regions, and especially also below the freezing point, and at different (regional and local) sites of a contamination event, and that such biodegradation takes place reliably, as rapidly as possible, and to a sufficient degree. Moreover, the improved bioremediation method is preferably simple and economical to carry out and makes it possible to minimize the number of personnel needed in the extreme ice regions. Another aspect is to provide preferred means for carrying out the bioremediation method, the use of which will allow the effectiveness of the bioremediation method to be significantly increased.

In one embodiment, the bioremediation method of the present invention uses a mixture of several different, cold-adapted autochthonous bacterial strains. Each of the bacterial strains used has different temperature and salt tolerance ranges, a different degradation spectrum, a different degradation activity, and a different oil-emulsifying capacity. This combination of different types of bacterial strains produces a mixture of complementary bacteria which have an extremely broad degradation range and allows a broad palette of petroleum hydrocarbons to be reliably biodegraded under greatly varying sea-ice conditions and contamination scenarios. Moreover, the cold-adapted bacterial strains used vary in their temperature and salt tolerance ranges so as to make the bioremediation method effective at all temperatures occurring in the natural habitat. However, all bacterial strains in the mixture have in common that they still exhibit activity (degradation or production of emulsifiers) at −3° C. Oil degradation at this low temperature is surprising to those skilled in the art and has not yet been reported in prior art literature. For this reason, the use of a bioremediation method in polar sea ice regions has heretofore been considered ineffective.

The bacterial mixture used in one embodiment of the bioremediation method according to the present invention may not only have a broader degradation spectrum than the individual organisms, but also may respond better to variations in the ecosystem, which is important because of the highly variable conditions in the ice. The broad activity range of the bacterial mixture ensures that minor (residual) oil spills can be reliably removed both in sea ice and in melting pools and in the adjacent water through bioaugmentation by distributing a single inoculum.

In such operations, the bacterial mixture may be used in high concentrations to compensate for the slow regeneration and reproduction in ice.

In one embodiment, the bacterial mixture can be prepared by combining bacterial strains which are enriched in mesocosm experiments over a period of 12 to 36 months and subsequently isolated. The mesocosms are prepared using ice from a potential contamination site, artificially contaminated with crude oil, supplied with nutrients, and incubated at −3° C. in such a way that the ice/water situation remains stable. It should be noted that it is not necessary at all to isolate specific bacterial strains according to the aforementioned procedure for each event in which the bioremediation method is to be used. Rather, a multiplicity of suitable bacterial strains can be obtained in exemplary mesocosm experiments and stored. In a particular event in which the bioremediation method is to be used, the appropriate bacterial strains can then be combined in a bacterial mixture individually according to the circumstances of use, and especially according to the location of use. This in fact allows for quick response to oil spills using the bioremediation method according to the present invention. The bacterial strains obtained in this manner have complementary physiological properties and, as a mixture, are capable of degrading oil under the highly varying salinity and temperature conditions typical of sea ice. The bioremediation method of the present invention can be made even more effective, more flexible, and more widely usable by adding other oil-degrading bacterial strains and/or by distributing hydrocarbon-degrading enzymes from such cold-adapted microorganisms.

In a preferred method of preparing the bacterial mixture ensures that, as a general principle, autochthonous bacterial strains; i.e., those which are indigenous to a particular habitat, are used. Therefore, in addition to removing minor oil spills, the bioremediation method of the present invention is particularly suited for removing residual contamination after the use of mechanical oil recovery methods or in-situ burning. The use of such methods results in the destruction of the natural sea-ice flora, which can be compensated for by inoculation with the oil-degrading bacterial mixture. The use of autochthonous sea-ice bacteria enables the natural microflora to regenerate after mechanical and/or physical treatment of the sea ice. Therefore, the bioremediation method of the present invention is extremely environmentally friendly. It removes oil spills and at the same time regenerates the natural microflora. Moreover, it uses environmentally friendly carrier materials.

In one embodiment, the bioremediation method of the present invention, along with the bacterial strains deposited with the DSMZ - Deutsche Sammlung von Mikroorganismen and Zellkulturen GmbH [German Collection of Microorganisms and Cell Cultures], Inhoffenstraβe 7B, 38124 Braunschweig, Germany, is particularly suitable for spills in Arctic sea ice and for oil which is rich in aliphatic compounds. The bacterial strains concerned are new bacterial strains which are taxonomically distinguished from the known bacterial strains and have a distinctly different physiology. To date, these specific microorganisms were not expected to be present in sea ice. However, the method is not limited to this particular bacterial mixture, but may be extended by adding other bacterial strains which can be obtained according to the described method, for example ones which are more specialized for degrading aromatic hydrocarbons (polyaromatic hydrocarbons) or heavy oils. Even when spills occur in the Antarctic region where, in accordance with the Antarctic Treaty System, only autochthonous Antarctic bacteria can be used, it is possible to employ autochthonous bacterial strains obtained using this method. The range of application of the bioremediation method of the present invention can be further extended by using cold-adapted enzyme compositions from the isolated bacterial strains, because then the influence of physical-chemical conditions on the degradation activity is less than with intact microorganisms. When using said cold-adapted enzyme compositions, the method can be used in all cold regions in limnic, marine, pelagic as well as in benthic environments; i.e., in all Antarctic habitats, and also in Arctic deep-sea sediments, where specific bacteria are active which are adapted to the high hydrostatic pressure, and even in permafrost soils.

Due to the special composition of the inoculum, the bioremediation method of the present invention can be individually matched to specific conditions. It should be noted that the method can be used once, and the inoculum can be distributed once after a spill has occurred. It will then work in situ without personnel, even if, for example, inoculated ice floes are carried away. However, it is also possible to make subsequent adjustments by re-inoculation with the same or different microorganisms (e.g., degraders of polyaliphatic hydrocarbons) or by adding additional nutrients. Re-inoculation is performed according to the quality and quantity of the hydrocarbons to be degraded and according to the environmental conditions, and has to be handled differently from case to case.

Further advantageous embodiments of the bioremediation method according to the present invention are described in the detailed description section. Particular examples which may be mentioned here are the immobilization of the inoculum on special carrier materials and the method of distributing the inoculum in a spill event. The complex bacterial mixture is immobilized on environmentally friendly carrier material, which is supplied with preferably inorganic nutrients or which itself acts a nutrient. Depending on the contamination and ice conditions, it is possible to use floating or non-floating, hydrophilic or hydrophobic carrier materials as well as oil-binding carrier materials. This carrier material can be placed directly on the sea ice, on the adjacent water, or under the sea ice. The inoculum can be distributed over the surface of the ice by ship using a water cannon, or by airplane. Distribution under the ice can also be accomplished by introducing or pumping the inoculum into the water column under the ice. Therefore, the bioremediation method of the present invention does not have the limitations of the mechanical methods (suitable only for small floes) and physical methods (suitable only for dense ice covers or nearly open water). If helicopters are used, the inoculum can be distributed even under most difficult ice conditions, such as dense ice coverage or ice-rise formation.

Specific embodiments of the claimed bioremediation method for accelerated biological degradation of petroleum hydrocarbons in polar ice regions, and of the claimed bacterial mixtures as means for carrying out the method will be described below in greater detail.

Table 1 shows a selection of suitable bacterial strains for preferred bacterial mixtures. The first six of said bacterial strains can be combined to form a base mixture of bacteria, which can be optimally adapted to a particular spill event, and thus be further improved in its degradation effectiveness, by adding the further five bacterial strains mentioned.

Table 2 illustrates the degradation of aliphatic components of crude oil (0.2%) by the preferred bacterial mixtures in gap water and in an Arctic sea-ice mesocosm setup.

In one embodiment, a sequence of basic, preparatory and executable steps is be carried out prior to the bioremediation method. These steps are listed below. It should be noted that the basic and preparatory steps can be omitted if suitable isolated bacterial strains or inocula are already available for a particular spill event.

enriching and isolating specific bacterial strains which under stable sea-ice conditions, i.e., even at temperatures of −3° C., emulsify crude oil and degrade components thereof in relatively short time;

combining different types of the obtained sea-ice bacterial strains so as to produce a mixture of complementary bacteria which allows the broadest possible palette of crude oil components to be biodegraded in as accelerated a manner as possible under greatly varying sea-ice conditions and contamination scenarios;

producing a sufficiently active biomass from the selected bacterial strains;

forming an inoculum by immobilizing the active biomass on a carrier material along with suitable nutrients; and distributing the inoculum to bring it into contact with the petroleum hydrocarbons to be degraded.

In order to obtain suitable bacterial strains, the Applicant extracted, for example, different ice cores of Arctic multiyear ice in the area northeast of Spitsbergen (79° to 81° N and 5° to 12° East) during September and October (summer) and during April and May (Winter). Equally, Antarctic sea ice was sampled from the Bellinghausen Sea (66-71° CS and 275-290° W) during April and May (autumn) In the home laboratory, the ice was crushed under sterile conditions and approximately five liters thereof were filled into sterile glass containers along with 10 liters of sterile polar water. Fresh and stored crude oil (0.1%) was distributed over the floating ice. The different mesocosms were supplied with different nutrients:

Inipol MS3000 fish meal inorganic nutrients consisting of $Na_2HPO_4$ 0.065 $gl^{-1}$, $NaNO_3$ 0.75 $gl^{-1}$, traces of $FePO_4$.

The experiments were incubated at −3° C. over a period of 36 months. Parallel experiments with melted ice were incubated at +4° C. After one and a half year, first material samples were taken, serially diluted, and 100 µl of each of the different dilution levels was spread on minimal agar. Prior to this, about 20 µl of crude oil was distributed over the agar plates. The plates were incubated at +4° C. until colonies became visible. These colonies were picked and restreaked until pure cultures were obtained. The different strains were taxonomically classified by ARDRA (Amplified rDNA Restriction Analysis), and the sequences of the 16S rRNA genes of the different groups were determined Moreover, the types were examined for their physiological characteristics, temperature response, and hydrocarbon degradation potential. Surprisingly, new, cold-adapted types of bacteria could be found which degrade hydrocarbons at −3° C. The similarity in sequence between the 16S rRNA genes of the strains and the most closely related type strains is indicated in Table 1.

Six different bacteria types, which differ from previously known microorganisms, can preferably be used to form the mixture. The indicated bacterial strains are preferably added in equal amounts. Depending on the particular circumstances of use, the bacterial strains that work best will be dominant in terms of development. Also surprisingly, combining different bacteria types of different temperature and salt tolerance and different degradation potential ultimately produced a bacterial mixture which, as a whole, is capable of developing, and of emulsifying and degrading crude oil under different ice conditions in an acceptable time.

The bacterial strains listed in Table 1 are deposited with the DSMZ. They can be stored as growing strain cultures in tubes in 10 ml of minimal medium ($KNO_3$ 0.75 g, $NH_4Cl$ 0.75 g, yeast extract 0.1 mg (Difco), traces of $FePO_4$, in 1 liter of 50% Arctic sea water) plus 20 µl of crude oil for about half a year at 1° C., or be preserved (e.g., MAST Cryobank System, −80° C., or freeze-drying). In order to use or inoculate the cultures, it is necessary to recover the strains from the preserved state or to use the strain cultures. When preserved material is used, such material must first be recultivated in a sea water/nutrient medium (5 g Bacto Peptone (Difco), 1g yeast extract (Difco) and traces of $FePO_4$ in 1 liter of 50% Arctic sea water or marine broth 2216 (Difco)) at 4° C. For the bacterial strains GH-10 (DSM 18952) and GH-11 (DSM 18953), a 10-fold diluted sea water/nutrient medium should be used, and 0.1% sterile crude oil should be added. Once sufficient growth is present (which takes about 2 days to 1 week, depending on the particular strain), these cultures are used to inoculate larger volumes (500 ml to about 10 L) of minimal medium ($KNO_3$ 0.75 g, $NH_4Cl$ 0.75 g, yeast extract 0.1 mg (Difco), traces of $FePO_4$, in 1 liter of 50% Arctic sea water) plus 0.2% (v/v) of oil. The strains are cultured under agitation (100 rpm) at 4° C. until a cell density of at least $1 \times 10^9$ cells per ml is reached (approximately 1 week). Due to the addition of crude oil, the strains become adapted to degrade hydrocarbons.

In one embodiment of the bioremediation method of the present invention, the microorganisms used and/or the enzyme compositions obtainable therefrom can be immobilized using carrier materials and brought to the site of contamination. To achieve optimal degradation of hydrocarbons, it is preferable to provide the microorganisms with nitrogen and phosphate sources. In order for the nutrients and microorganisms to reach and remain at the site of contamination together, it is preferable to use environmentally friendly carrier materials. The selection of the carrier material can be done taking into account the different sea-ice contamination scenarios. Carrier materials used may include hydrophobic and hydrophilic materials, which are, or are not, capable of floating, respectively. It is preferable for the bacterial mixture be immobilized on two different carrier materials and distributed in this form, so that different locations of use can be reached. Preferably, the following materials may be used:

Carrier Material 1:

Based on the particulate material described in U.S. Pat. No. 5,954,868, carrier material 1 comprises a core of nutrients; e.g., $NH_4H_2PO_4$ and $FeSO_4$ in an ammonium/phosphate/iron ratio of 90:8:2, and is covered by oleophilic components, such as saturated and unsaturated fatty acids (e.g., oleic acid, stearic acid and/or palmitic acid). Carrier material 1 is oleophilic and capable of floating. The organic component is combined with an inorganic component. After use, the material does not leave any residues.

Carrier Material 2:

Based on the "Bio-Sep technology" (University of Tulsa, Okla. 74104, USA), carrier material 2 comprises beads made of 25% of aramid polymer (Nomex) and 75% of activated carbon (PAC) and having a diameter of 3-4 mm and a porosity of 75%. The mean pore diameter is 1.9 µm. The beads are surrounded by a membrane similar to an ultrafiltration membrane. The nutrients are absorbed by the beads, and the organisms colonize within the beads. To date, the beads have been used for cleaning up groundwater. Carrier material 2 is oleophilic and capable of floating. Both organic and inorganic nutrients can be used. However, one potential disadvantage is that aramid is a plastic and remains in the ecosystem after its use.

Carrier Material 3:

Based on German Laid-Open Application No. DE 199 54 643 A1, carrier material 3 is based on an oil binder produced from fiber-forming proteins. The material is loaded with nutrients, it absorbs oil, is capable of floating and, therefore, is preferable for use when there is free water or when oil has gotten under the ice.

Carrier Material 4:

Carrier material 4 is based on fish meal to which is added polysorbate 80 (polyoxyethylene sorbitan monooleate, commercially also known as Tween® 80), which is a nonionic surfactant used in cosmetics, drugs, feeds and, in particular, as an emulsifier in foods. Polysorbate acts as an emulsifier, so that the carrier material attaches to the spilled oil. Carrier material 4 is particularly suited for contaminations on the surface of the sea ice, but also for contaminations inside the sea ice.

Carrier Material 5:

Carrier material 5 is based on sawdust (0.3-1 mm particle diameter) soaked with nutrients ($NH_4H_2PO_4$ 0.065 $gL^{-1}$, $NaNO_3$ 0.75 $gL^{-1}$ and traces of $FeCl_3$). Sawdust is hydrophilic and therefore does not float on water. Hence, carrier material 5 is particularly suited for minor spills on the ice surface, but also for contaminations inside the sea ice, because the sawdust particles can sink into deeper ice layers.

In order to immobilize the cells, the individual, large-volume cultures (in minimal medium with oil) of the various bacterial strains are added together and mixed in a sterile container. After that, the mixture is distributed into a number of containers equal to the number of different carrier materials to be used. Per 1 liter of the mixture, 20 g of sterile carrier material is added, and the preparation is then agitated (90 rpm) for 3 days at 4° C. so as to allow the cells to attach to the carrier material. After that, the carrier material can be substantially removed from the nutrient solution, depending on the distribution method. The material can be distributed in this form over the ice by spraying, sprinkling, pouring and may even be pumped under the ice, depending on the type of equipment available and on the particular circumstances of use. For spray application, it is recommended not to separate the carrier material from the nutrient solution, but to spray it out along with the nutrient solution. The individual distribution methods must be matched to the carrier materials. In order to protect the cold-adapted microorganisms, it is recommended never to store or use the inoculum above refrigerator temperature (+7° C.). Above this temperature, the microorganisms could be damaged. For example, their degradation activity could be significantly reduced.

In the event of a large-scale oil spill, large quantities of biomass are distributed. To this end, the culture is first upscaled. To allow quick response to an acute oil spill, cell masses are held available for use in freeze-dried form or frozen in antifreeze. In this connection, it should be taken into account that the preservation methods may damage part of the cells. Therefore, the cells are reactivated in minimal medium with crude oil during a short incubation phase of three days prior to distribution.

Although in other habitats, inoculation of oil-degrading organisms has largely not been successful so far, and although the hostile habitat of sea ice is rather not a suitable place for bioremediation and bioaugmentation, it turned out that aliphatic oil components, even long-chain ones, were significantly degraded in oil-contaminated sea-ice mesocosm preparations and in gap water (liquid layer typically present in Antarctic summer ice) using the bioremediation method according to the present invention, as will be described in the examples below. The results of the demonstrative examples described below are shown in Table 2.

Demonstrative Example 1

Sawdust loaded with minimal medium and the mixture of oil-degrading sea-ice bacteria was distributed in gap water that had formed in the Antarctic sea ice and which had been artificially contaminated with crude oil. After half a year using the bioremediation method of the present invention, all alkanes were completely degraded, except for a small fraction of very long-chain aliphatics. In the control preparations with only nutrients and those without addition of nutrients, degradation took place to a much lesser extent or not at all.

Demonstrative Example 2

In a mesocosm experiment, the surface of Arctic sea ice (winter experiment) and of Antarctic sea ice (summer) was contaminated with oil from the Barents Sea having a high content of aliphatics. Oil-degrading bacteria, which had been immobilized on fish meal, were distributed over the oil spill. In these preparations, crude oil could be degraded using the bioremediation method according to the present invention, while in untreated oil-contaminated ice, no degradation could be observed.

As regards the implementation of the bioremediation method according to the present invention, the following scenarios can be described:

Scenario 1:

In the event of an oil spill where larger amounts of hydrocarbons are released into a sea-ice covered area, large amounts of the oil can be removed using physical or mechanical methods, depending on the ice conditions. Using such methods, large amounts of oil are indeed removed, but hydrocarbon residues remain in the ice, leaving the ecosystem destroyed, so that the hydrocarbons can no longer be degraded by the organisms formerly naturally found in the ice. By distributing a mixture of organisms and nutrients as set forth in the present invention, it is possible to quickly initiate a biological degradation process, so that the remaining hydrocarbons can also be completely removed from the ecosystem within an acceptable time-frame. The bacterial mixture and nutrients on the carrier material can be distributed over large ice surfaces and water surfaces between ice floes by spraying using a water cannon, or from a helicopter. Hydrophobic carrier material will attach to the hydrocarbons present, thereby allowing direct contact with the microorganisms and nutrients. The subsequent oil-degradation process will then occur without requiring any human intervention; i.e., there is no need to further monitor the ice floe. This is particular important because ice floes can very quickly drift away and break apart.

Scenario 2:

In the event of a minor spill of hydrocarbons, the same applies as above, except that there is no need for prior cleaning using physical or mechanical methods.

Scenario 3:

In the event of a leak occurring, for example, in a pipeline laid on the bottom of the sea in ice-covered waters (as is already the case in the Arctic shelf regions which are covered with ice during winter and autumn), oil will rise up through the water column and accumulate under the ice, where it quickly becomes incorporated into the ice and, thus, can be carried far away with drifting ice floes. In springtime, the oil will rise to the surface through cracks and brine channels.

By distributing the carrier material containing the bacteria and nutrients into the water column under the ice in accordance with the bioremediation method of the present invention, hydrophobic carrier material will come into contact with the oil also at the underside of the ice and be incorporated into the ice, so that the degradation of the hydrocarbons can start already in the ice column. The carrier material described above will rise to the surface of the ice along with the oil. Again, the advantage of this use is that the bacterial mixture is distributed once after a spill and will then work in situ, even if the ice floe is carried away.

Prior to the filing date of the German patent application (DE 10 2007 003 644.4, 2007 Jan. 21) that establishes priority of invention, 11 bacterial strains were deposited on Dec. 22, 2006 with the Deutsche Sammlung von Mikroorganismen and Zellkulturen GmbH [German Collection of Microorganisms and Cell Cultures] (DSMZ) at Inhoffhofenstr. 7B, D-38124 Braunschwieg, Germany in accordance with the Budapest Treaty on the International Recognition of the Deposit of Microorganisms for the Purposes of Patent Procedure. Accordingly, 11 deposit receipts and 11 viability statements were submitted (each in both German and English). The taxonomic description, identification number given by the depositor (GH1-11) and accession number given by the International Depository Authority (DSM 18943-18953) for each of the 11 bacterial strains are as follows: *Rhodococcus* GH-1 deposited with the DSMZ and assigned accession number DSM 18943; *Dietzia* GH-2 deposited with the DSMZ and assigned accession number DSM 18944; *Marinobacter* GH-3 deposited with the DSMZ and assigned accession number DSM 18945; *Shewanella* GH-4 deposited with the DSMZ and assigned accession number DSM 18946; *Marinomonas* GH-5 deposited with the DSMZ and assigned accession number DSM 18947; *Pseudoalteromonas* GH-6 deposited with the DSMZ and assigned accession number DSM 18948; *Psychrobacter* GH-7 deposited with the DSMZ and assigned accession number DSM 18949; *Jannaschia* GH-8 deposited with the DSMZ and assigned accession number DSM 18950; *Marinobacter* GH-9 deposited with the DSMZ and assigned accession number DSM 18951; *Pseudomonas* GH-10 deposited with the DSMZ and assigned accession number DSM 18952; and *Oleispira* GH-11 deposited with the DSMZ and assigned accession number DSM 18953.

The present invention is not limited to the embodiments described herein; reference should be made to the appended claims.

TABLE 1

| Name of Strain / DSMZ Deposit Number / Deposit Date | Characterization | Degree of Relationship*) | Origin |
|---|---|---|---|
| Rhodococcus GH-1 DSM 18943 DSMZ Dec. 22, 2006 | broad degradation spectrum | 98% R. yunna-nensis | Arctic summer ice |
| Dietzia GH-2 DSM 18944 DSMZ Dec. 22, 2006 | broad degradation spectrum and broad temperature and salinity spectra | 99.5% D. maris | Arctic winter ice |
| Shewanella GH-4 DSM 18946 DSMZ Dec. 22, 2006 | limited degradation spectrum, short-chain alkanes, but very fast growth at very cold temperatures | 98% S. livingstonensis | Arctic summer ice |
| Marinobacter GH-9 DSM 18951 DSMZ Dec. 22, 2006 | good degradation spectrum, very fast growth | 95% M. aquaeolei VT8 | Antarctic summer ice |
| Pseudomonas GH-10 DSM 18952 DSMZ Dec. 22, 2006 | broad degradation spectrum, particularly good interaction | 94% P. pertucinogena | Arctic summer ice |
| Oleispira GH-11 DSM 18953 DSMZ Dec. 22, 2006 | broad alkane-degradation spectrum at very low temperatures, sensitive strain | 99.6% O. antarctica | Arctic winter ice |
| Additional Strains | | | |
| Marinobacter GH-3 DSM 18945 DSMZ Dec. 22, 2006 | very broad degradation spectrum, psychrotolerant | 96% M. aquaeolei VT8 | Arctic winter ice |
| Marinomonas GH-5 DSM 18947 DSMZ Dec. 22, 2006 | degrades specific hydrocarbons, fast growth at temperatures below freezing | 98% M. protea | mixed ice |
| Pseudoalteromonas GH-6 DSM 18948 DSMZ Dec. 22, 2006 | degrades specific hydrocarbons, very broad temperature spectrum | 99.6% P. elyakovii | Arctic summer ice |
| Psychrobacter GH-7 DSM 18949 DSMZ Dec. 22, 2006 | degrades specific hydrocarbons, very broad salinity spectrum | 98% P. glacincola | Arctic summer ice |
| Jannaschia GH-8 DSM 18950 DSMZ Dec. 22, 2006 | broad degradation spectrum, slow growth | 94% J. rubra | Antarctic summer ice |

*)The similarity in sequence of the 16S rRNA gene to the most closely related type strain or well-described strain

TABLE 2

| Sample | after half a year using bioaugmentation plus nutrient addition | | after half a year using only nutrient addition | | after half a year without using any additives | |
|---|---|---|---|---|---|---|
| | n-alkanes | pristanes, phytanes | n-alkanes | pristanes, phytanes | n-alkanes | pristanes, phytanes |
| gap water from Antarctic sea ice | $C_{14}$-$C_{15}$ (g)#) $C_{16}$-$C_{19}$ (g) $C_{20}$-$C_{24}$ (g) $C_{24}$-$C_{30}$ (t) | pr ph (l) | $C_{14}$-$C_{15}$ (g) $C_{16}$-$C_{19}$ (t) $C_{20}$-$C_{24}$ (k) $C_{24}$-$C_{30}$ (k) | pr ph (k) | $C_{14}$-$C_{15}$ (l) $C_{16}$-$C_{19}$ (k) $C_{20}$-$C_{24}$ (k) $C_{24}$-$C_{30}$ (k) | pr ph (k) |
| mesocosm experiment using Arctic sea ice | $C_{14}$-$C_{15}$ (g) $C_{16}$-$C_{19}$ (g) $C_{20}$-$C_{24}$ (g) $C_{24}$-$C_{30}$ (t) | pr ph (l) | $C_{14}$-$C_{15}$ (g) $C_{16}$-$C_{19}$ (t) $C_{20}$-$C_{24}$ (k) $C_{24}$-$C_{30}$ (k) | pr ph (k) | $C_{14}$-$C_{15}$ (l) $C_{16}$-$C_{19}$ (k) $C_{20}$-$C_{24}$ (k) $C_{24}$-$C_{30}$ (k) | pr ph (k) |

)level of degradation: completely (g), partially (t), slightly (l), no degradation observed (k)

What is claimed is:

1. An enviromental friendly carrier material comprising a bacterial mixture capable of accelerated biological degradation of petroleum hydrocarbons in a sea ice-covered polar region, the bacterial mixture comprising a plurality of isolated different cold-adapted autochthonous bacterial strains each having petroleum hydrocarbons degrading activity at an ambient temperature of −3° C. and each having a different temperature tolerance range, a different salinity tolerance range, a different petroleum hydrocarbons degradation spectrum, and a different capacity to emulsify oil, wherein the bacterial mixture is immobilized on the carrier material, and wherein bacterial the bacterial mixture comprises at least one isolated bacterial strain selected from the group consisting of Rhodococcus GH-t deposited with the German Collection of Microorganisms and Cell Cultures Depository in Braunschweig, Germany (DSMZ) and assigned accession number DSM 18943; *Dietzia* GH-2 deposited with the DSMZ and assigned accession number DSM 18944; *Shewanella* GH-4 deposited with the DSMZ and assigned accession number DSM 18946; *Marinobacter* GH-9 deposited with the DSMZ and assigned accession number DSM 18951; *Pseudomonas* GH-10 deposited with the DSMZ and assigned accession number DSM 18952; *Oleispira* GH-11 deposited with the DSMZ and assigned accession number DSM 18953.

2. The carrier material having the bacterial mixture according to claim 1, wherein bacterial strains comprise dominant bacterial strains that are isolated after enrichment in a laboratory mesocosm setup over a period of 12 to 36 months, the mesocosm being prepared with sea ice from a current or potential contamination site, artificially contaminated with crude oil, supplied with nutrients, and incubated at −3° C.

3. The carrier material according to claim 1, wherein the bacterial mixture further comprises at least one isolated additional bacterial strain to broaden an overall degradation spectrum and enhance an overall oil emulsifying capacity, the at least one additional bacterial strain being selected from the group consisting of: *Marinobacter* GH-3 deposited with the German Collection of Microorganisms and Cell Cultures Depository in Braunschweig. Germany (DSMZ) and assigned accession number DSM 18945; *Marinomonas* GH-5 deposited with the DSMZ and assigned accession number DSM 18947; *Pseudoalteromonas* GH-6 deposited with the DSMZ and assined accession number DSM 18948; *Psychrobacter* GH-7 deposited with the DSMZ and assigned accession number DSM 18949; and *Jannaschia* GH-8 deposited with the DSMZ and assigned accession number DSM 18950.

4. An enviromental friendly carrier material comprising a bacterial mixture capable of accelerated biological degradation of petroleum hydrocarbons in a sea ice-covered polar region at an ambient temperature of −3° C., the bacterial mixture being obtained by isolating dominant bacterial strains that are enriched in a laboratory mesocosm setup over a period of 12 to 36 months, the mesocosm being prepared with sea ice from a current or potential contamination site, artificially contaminated with crude oil, supplied with nutrients, and incubated at −3° C., wherein the bacterial mixture immobilized on the carrier material.

5. An enviromental friendly carrier material comprising a bacterial mixture capable of accelerated biological degradation of petroleum hydrocarbons in a sea ice-covered polar region, the bacterial mixture comprising a plurality of isolated different cold-adapted autochthonous bacterial strains each having petroleum hydrocarbons degrading activity at an ambient temperature of −3° C., and each having a different temperature tolerance range, a different salinity tolerance range, a different petroleum hydrocarbons degradation spectrum, and a different capacity to emulsify oil, wherein the bacterial mixture immobilized on the carrier material, and wherein the bacterial mixture comprises each of: *Rhodococcus* GH-t deposited with the German Collection of Microorganisms and Cell Cultures Depository in Braunschweig, Germany (DSMZ) and assigned accession number DSM 18943; *Dietzia* GH-2 deposited with the DSMZ and assigned accession number DSM 18944; *Shewanella* GH-4 deposited with the DSMZ and assigned accession number DSM 18946; *Marinobacter* GH-9 deposited with the DSMZ and assigned accession number DSM 18951; *Pseudomonas* GH-10 deposited with the DSMZ and assigned accession number DSM 18952; *Oleispira* GH-11 deposited with the DSMZ and assigned accession number DSM 18953.

* * * * *